United States Patent [19]

Smith

[11] Patent Number: 4,808,186

[45] Date of Patent: Feb. 28, 1989

[54] CONTROLLED STIFFNESS FEMORAL HIP IMPLANT

[75] Inventor: Todd S. Smith, Warsaw, Ind.

[73] Assignee: Boehringer Mannheim Corporation, Indianapolis, Ind.

[21] Appl. No.: 151,627

[22] Filed: Feb. 2, 1988

[51] Int. Cl.$^4$ ................................................ A61F 2/32
[52] U.S. Cl. ...................................... 623/23; 623/18; 128/92 YZ
[58] Field of Search ....................... 623/18, 20, 22, 23, 623/19; 128/92 Y, 92 YZ, 92 YY, 92 YE, 92 YF, 92 YP

[56] References Cited

U.S. PATENT DOCUMENTS

| | | | |
|---|---|---|---|
| Re. 28,895 | 7/1976 | Noiles | 623/22 |
| 4,287,617 | 9/1981 | Tornier | 623/23 |
| 4,475,545 | 10/1984 | Ender | 128/92 YY |
| 4,623,353 | 11/1986 | Buechel et al. | 623/23 |
| 4,683,878 | 8/1987 | Carter | 128/92 YP |
| 4,743,263 | 5/1988 | Petrtyl et al. | 623/23 |

FOREIGN PATENT DOCUMENTS 562273  8/1977  U.S.S.R. .......................... 128/92 YZ

OTHER PUBLICATIONS

*Cementless Fixatin of "Isoelastic" Hip Endoprostheses Manufactured from Plastic Materials,* Clinical Orthopaedics, vol. 176, Morscher et al., 6/1983, pp. 77–87.

Primary Examiner—Richard J. Apley
Assistant Examiner—David J. Bender
Attorney, Agent, or Firm—Perman & Green

[57] ABSTRACT

A controlled stiffness elongated implant for use in the hip or other appropriate body joint. In the instance of the hip, a ball member fixed to the femur is rotatably engaged with a cup-shaped socket member fixed to the acetabulum of the pelvic bone. The ball member is mounted on one end of a femoral component which has an elongated stem receivable in the intramedullary canal of the femur. The stem has a longitudinal channel therein which lies generally in the coronal plane when the stem is in the implanted condition. The thickness of the stem laterally of the channel is variable between the proximal and distal ends so as to affect the moment of inertia at any given location along the length of said stem to thereby achieve stem flexibility which substantially correlates to the flexibility of the bone.

10 Claims, 4 Drawing Sheets

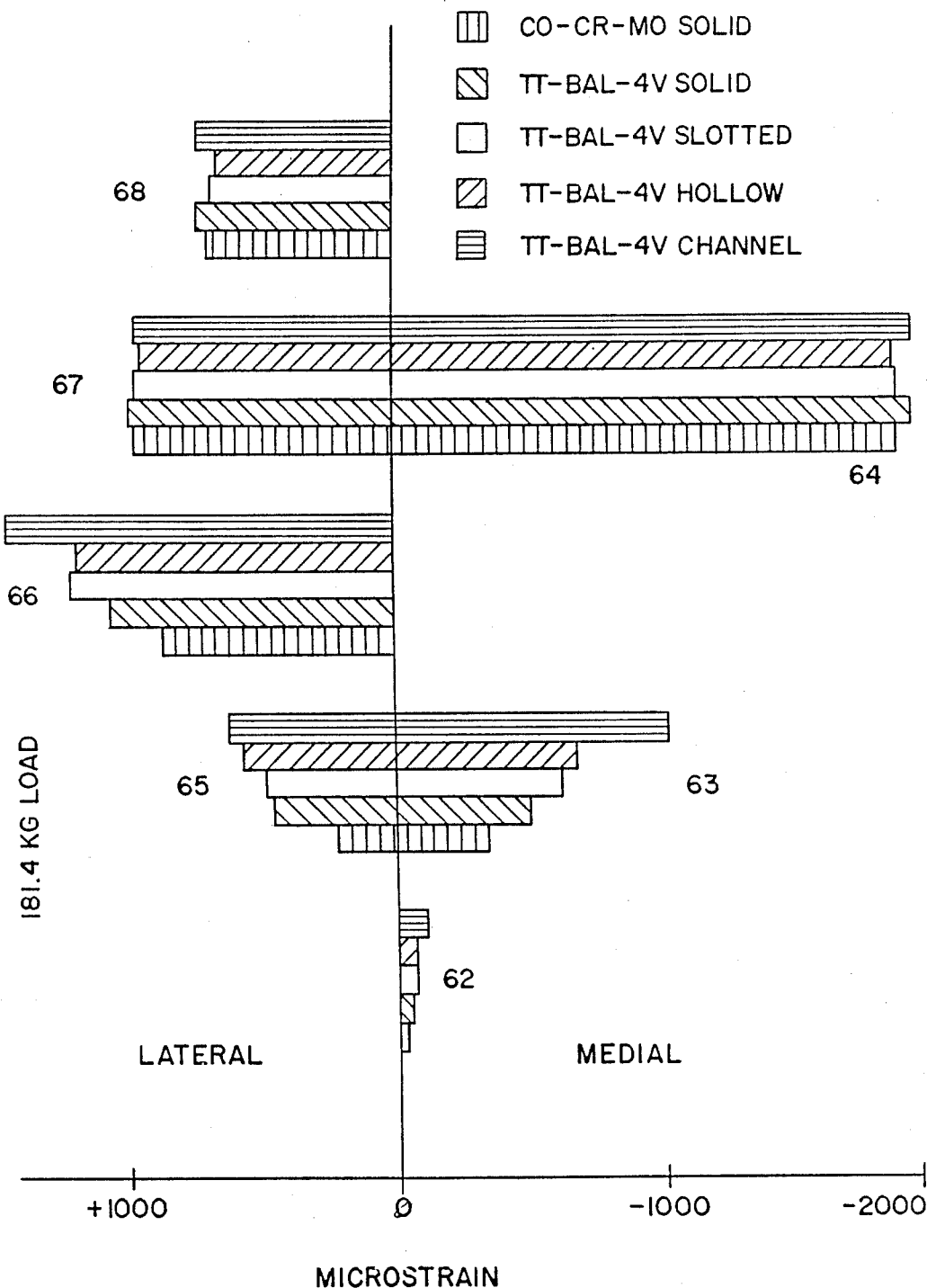

CONTROLLED STIFFNESS FEMORAL HIP IMPLANT

BACKGROUND OF THE INVENTION

I. Field of the Invention

The present invention relates generally to a femoral hip prosthesis and, more particularly, to a femoral component which can be stress tailored to the femur in which it is implanted.

II. Description of the Prior Art

Based on the precepts of Wolff's Law which states that bone tissue will remodel in direct relation to the stress applied to it, it is desirable to stress bone at an optimal level to minimize and control remodeling. Usually some degree of proximal femur bone remodeling accompanies total hip replacement. Due to mechanical stiffness, metallic implants typically stress protect the proximal bone to some extent. In patients with relatively large intramedullary canals which require a large diameter implant for optimal fit, stress protection may be particularly problemsome. In the most extreme case, the proximal femoral bone may resorb to a small fraction of its original mass, possible causing a loss of support of the implant or implant breakage.

It is unfortunate that implant flexural stiffness increases at an exponential rate, typically at powers between two and four, depending upon implant geometry, relative to linear increases in implant dimension. Further aggravating the situation is the fact that there is little correlation between the size of the patient and the diameter of the intramedullary canal. That is, a small, relatively light person may have a femur with a large diameter canal and a much larger person may have a femur with a smaller diameter canal. Therefore, it is desirable to produce an implant, especially a large diameter implant, with greatly reduced stiffness in relation to its mass.

This can be accomplished in several ways. For example the use of materials which are inherently less stiff, that is, possess a lower flexural modulus might be considered. Thus, the use of titanium alloy or a carbon fiber reinforced polymer composite in lieu of the stiffer cobalt-chrome alloy might be considered. An implant can also be hollowed out. This method is marginally effective, however, due to the fact that the centrally located material contributes little to the stiffness of the implant. For example if an implant with a round stem of 16 mm diameter is hollowed to a wall thickness of only 2 mm, the resulting decrease in flexural stiffness is only 32% while the decrease in mass is 56%. Interestingly, a 16 mm diameter stem is 6.5 times stiffer than the 10 mm diameter stem.

Morscher and Dick reported on nine years of clinical experience with a so-called "isoelastic" shaft prosthesis manufactured using polyacetal resin to transmit forces from the pelvis through the femoral head and neck into the femur in their paper: "Cementless Fixation Of 'Isoelastic' Hip Endoprostheses Manufactured From Plastic Materials", *Clinical Orthopaedics*, June, 1983, volume 176, pages 77–87. They stated: "The optimal fixation of an implant depends mainly on its design and material. The insertion of an artificial joint induces remodeling of the bony structures. If stability is not achieved, the implant sooner or later will loosen. The elasticity, and consequently the deformation, of an implant depend on the elastic modulus of the material and on the prosthetic design. By adjusting the physical characteristics of the foreign material to that of the bone tissue, as well as the design of the prosthesis to the femoral shaft, the entire system would have the same elasticity as a normal femur. A more elastic hip endoprosthesis also may act as a shock absorber during walking, particularly in the hell/strike and toe/off phases."

They proceeded to explain that this was the concept of the "isoelastic" hip endoprosthesis manufactured by Robert Mathys and implanted in 1973. In this instance, the prosthesis was composed of polyacetal resin which has an elasticity modulus approaching that of bone tissue, good durability, and tenacity for highly stressed components in combination with good tissue tolerance. To achieve the acquired structural strength in the neck portion, the component was reinforced by a metallic core that was tapered toward the tip to increase the elasticity of the stem, thereby allowing the stem of the prosthesis to follow the deformation of the bone. In commenting on the design, the authors further stated: "Isoelasticity implies the optimum approximation of the physical characteristics of an implant to those of the bone. An ideal isoelasticity, however, can never be achieved, since bone is anisotropic and the alloplastic materials used for joint arthroplasty show isotropic properties. In addition, there is no adaptation of the structures to the forces acting on the hip, as in the case in viable bone. Moreover, the variety of individual forms and strengths of human bone can never be imitated by an artificial joint. Use of more elastic materials, however, should avoid the disadvantages of the rigid materials used to date."

U.S. Pat. No. 4,287,617 to Tornier discloses a hip prosthesis with a femoral stem which provides a measure of the elasticity spoken of by Morscher and Dick. A transverse section of the Tornier stem is in the form of a substantially rectangular tube of which one of the small sides is virtually cut away so as to leave a very large slot. The C-shaped section thus obtained is said to exhibit excellent transverse elasticity which facilitates the positioning of the pin in the medullary cavity by insertion. Other stated advantages are that the pin is not as heavy as solid designs, and that the cavity encourages bone growth.

SUMMARY OF THE INVENTION

An alternate approach to the foregoing is the subject of this disclosure. Briefly stated, the medial side of the length of the implant is milled out to form a channel shaped stem cross section. The amount of material removed determines the resulting decrease in stiffness of the implant. The outside geometry remains substantially unchanged with the exception of the open channel on the medial side of the implant.

Because of the reduction of the moment of inertia of the implant stem, it is more flexible. It also exhibits higher stem stresses upon loading of the implant. Therefore, a careful balance must be achieved between the amount of material removed from the stem and the expected stress levels expected by the particular size implant.

The resulting longitudinal channel lies generally in the coronal plane when the stem is in the implanted condition. The depth of the channel is variable between the proximal and distal ends of the femoral implant so as to affect the moment of inertia at any given location along a length of the stem to thereby achieve an optimal stem flexibility. That is, the stem is so formed that at specified locations along its length, it substantially correlates to the flexibility of the femur itself.

However, for at least two excellent reasons, it is desirable that when the channel is formed, the resultant dimension of the stem in the lateral/medial direction be no smaller than approximately 70% of the original dimension or of the dimension in the anterior/posterior plane assuming the cross sectional shape is round. Reasons supporting this desirable relationship include the fact that the stem may otherwise lose its fitting relationship in the intramedullary canal, which is substantially round in cross section. Furthermore, the greater the width of the canal, the sharper become the longitudinal edges of the stem which are produced adjacent the channel. These could undesirably cut into the bone, traumatizing the bone and causing pain as well as a high point loading of the bone, possibly causing it to be chiseled away. Indeed, to preclude these potential difficulties, it is preferable that the final dimension in the lateral/medial direction will be no less than 85% of the dimension in the anterior/posterior plane.

The femoral stem exhibiting the qualities of the invention may be composed of any of the common materials generally employed for implants including titanium, titanium alloy, cobalt-chromium alloy, and composite materials. However, the use of ceramics and sintered powdered metal constructions may also be considered.

The channel itself may be formed during a molding process or by mechanical or chemical milling procedures, or in any other suitable fashion.

Also, according to the invention, it is considered that there would be a standard size range of stems, perhaps seven to ten different sizes varying in outer diameter, length, depth of the channel, the amount of the taper from the proximal to the distal ends of the stem. The closest sizes would be determined radiographically prior to surgery, although the final size decided upon for implanting could be finally chosen during surgery.

Other and further features, objects, advantages, and benefits of the invention will become apparent from the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention and, together with the description, serve to explain the principles of the invention in general terms. Like numerals refer to like parts throughout the disclosure.

BRIEF DESCRIPTION OF THE DRAWINGS

FIG. 6 is a bar chart which presents in a different manner the information presented in FIG. 5.

DETAILED DESCRIPTION OF THE PREFERRED EMBODIMENT

Figure 1:
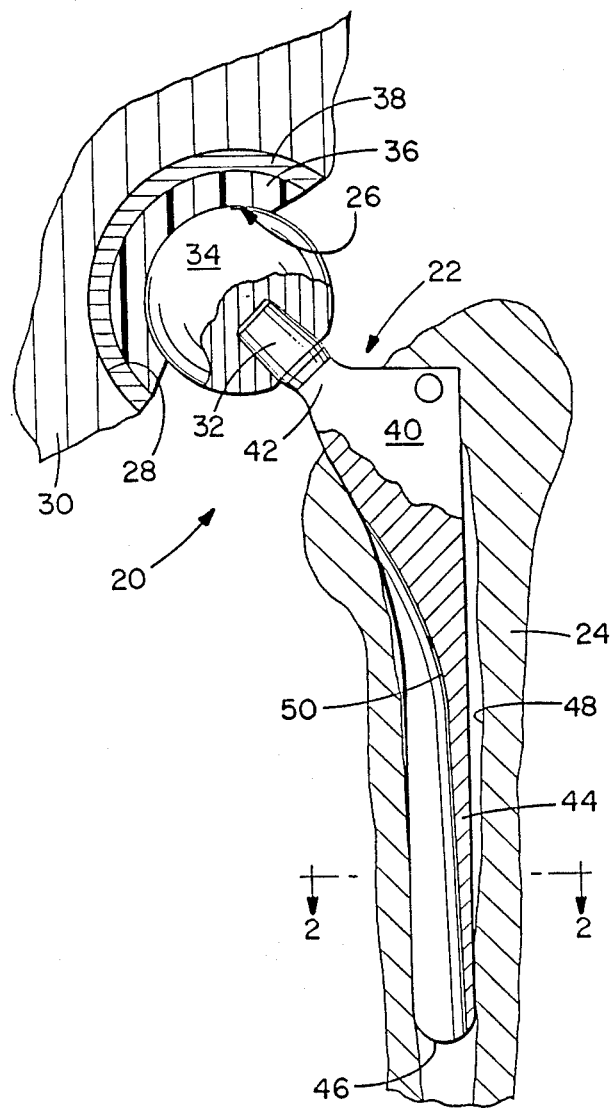
FIG. 1 is a side elevation view, certain parts being cut away and shown in section, of a hip prosthesis, including a femoral component embodying the invention.

Turn now to the drawings, and initially to FIG. 1, which illustrates a hip prosthesis 20 which embodies the invention. As illustrated, a femoral component 22 is suitably implanted in the femur 24 and is cooperatively engaged with an acetabular component 26. The latter component is suitably implanted in the acetabulum 28 of the pelvis 30. In customary fashion, the femoral component 22 has a taper 32 at its extreme proximal end adapted to fittingly receive thereon a ball 34. In turn, the ball is rotatably engaged with a bearing 36 of the acetabular component 26 which may be supported in a metal cup 38 which is generally fixed to the pelvis 30. The femoral component 22 further includes a shoulder 40, with the taper 32 being joined to the shoulder via a neck 42. A stem 44 extends away from the shoulder 40 to a distal or tip end 46.

Figure 2:
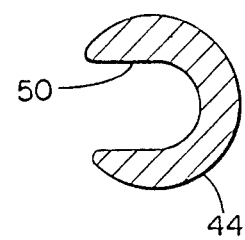
FIG. 2 is a cross section view taken generally along line 2—2 in FIG. 1.

In a customary manner, the stem 44 is received in the intramedullary canal 48 of the femur 24. The stem 44 is formed with a longitudinal channel 50 which lies generally in the coronal plane of the body of the person in whom the prosthesis is implanted. The depth of the channel 50 (see especially FIG. 2) is variable between the proximal and distal ends of the femoral component 22, its purpose being to affect the moment of inertia of the femoral component at any given location along the length of the stem 44 to thereby achieve an optimal stem flexibility.

Figure 3:
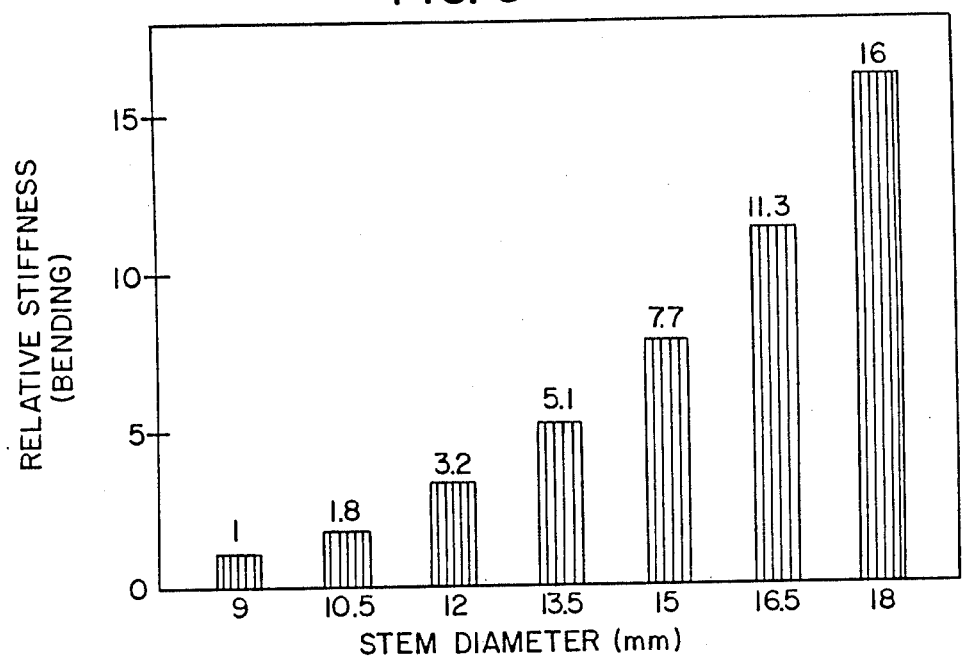
FIG. 3 is a bar graph indicating relative stiffness of a series of stems of varying diameters for femoral components which are currently available commercially.

It was previously mentioned as being unfortunate that implant flexural stiffness increases at an exponential rate, typically at powers between two and four, depending upon implant geometry, relative to linear increases in implant dimension. Graphic proof of this statement is presented in FIG. 3 which is a bar graph indicating relative stiffness of a series of stems of varying diameters which are currently available for implanting. It is noteworthy that the 18 millimeter diameter stem exhibits 16 times the stiffness of the 9 millimeter diameter stem. The invention serves to avoid this exponential increase and limits the increase in stiffness to an approximately linear relationship with increasing stem diameter.

It will be appreciated that femoral hip implants are subjected predominately to a bending mode of loading based on biomechanical analyses. This loading gives rise to the highest stem stresses according to the formula:

$$S_{max} = Mc/I$$

where $S_{max}$ is the maximum stress at any location of interest along the stem; M is the bending moment imparted to the structure at the particular location of interest; c is the distance from the neutral axis to the location of interest; and I is the moment of inertia about an anterior-posterior axis, a geometrical consideration.

If the maximum allowable stress based on material limitations is known and if the loading condition of the implant based on biomechanical analyses is known, one can then solve for the necessary moment of inertia via the rearrangement of the above equation, as follows:
$$I = Mc/S_{max}$$

It has been mentioned as desirable to limit the width of the femoral component 22 in the region of the channel 50 to no less than 70% the dimension of a similarly shaped stem in that plane not formed with the channel. As previously mentioned, the reasons for this relationship include a desire to maintain the fit of the stem 44 within the intramedullary canal 48 as well as the prevention of sharp edges 52 which would be produced adjacent the channel in the event the channel is made excessively wide. This is most clearly seen in FIG. 4 which is representative of the stem 44 having a circular cross section and before it is formed with the channel 50.

Based on the general criterion as just mentioned of maintaining the lateral-medial width of the femoral component 22 to no less than 70% of the anterior-posterior dimension, in the event the stem 44 is of circular cross section, or 70% of the lateral-medial width of an unchanneled stem, one can determine the channel depth necessary to satisfy the geometrical considerations of the moment of inertia, I. In the instance of stem 44 of circular cross section (see FIG. 4), the moment of inertia is determined as follows:
$$I = \pi r^4/4$$
where r equals the stem radius.

Now, at each location along the length of the stem, the depth of the channel 50 to be formed can be determined. In the first instance, the desired channel width is determined which assures the lateral-medial dimension being no less than 70% of the original dimension. Thus, the channel width as represented by the reference numeral 54 (FIG. 4) is a known quantity.

Furthermore, stiffness of the desired implant at any given location along its length is a known quantity. This is determined from clinical experience. Stiffness is proportional to the moment of inertia, I, and therefore increases in proportion to the fourth power of the diameter of the stem. However, according to the invention, this increase would be limited to a fraction of what it would be for a solid implant and this fractional increase is achieved by means of the channel 50.

Figure 4:
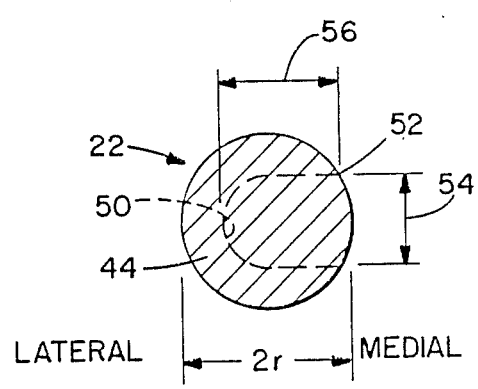
FIG. 4 is a cross section view of the stem of a femoral component having a circular cross section and awaiting modification according to the invention.

With the aid of FIG. 4, it should be clear that
$$I_{implant\ w/channel} = I_{circle} - I_{channel}$$

Based on the foregoing, the magnitude of $I_{implant}$ and of $I_{circle}$ are known, requiring that $I_{channel}$ be determined. However, $I_{channel}$ is a function of the width and depth of the channel. It was previously stated that the channel width 54 is a known quantity, requiring a solution, now, of the only remaining unknown, that is, the depth of the channel as represented by the reference numeral 56. If the channel, viewing FIG. 4, is approximated, in cross sectional shape with being that of a rectangle, then:
$$I_{channel} = bh^3/12$$
where b is the channel width 54 and h is the channel depth 56. This latest equation can be rearranged in order to solve for the quantity h. Of course, it will be recognized that by reason of the fact that the moment of inertia $I_{channel}$ is proportional to the third power of channel depth 56, the channel depth is a very critical value indeed.

Thus, $I_{implant\ w/channel}$ is determined for various channel depths used to satisfy the aforementioned equation, namely:
$$S_{max} = Mc/I$$

In the course of proving the desirability of the invention, five similarly sized femoral implants of different design were tested. Both the implant material and geometry was modified in four of the five implants used. A standard 15 mm AML® femoral component (a product of DePuy Division of Boehringer Mannheim Corporation of Warsaw, IN) which was fabricated from Co-Cr-Mo alloy was used as the control. The four experimental devices were fabricated from Ti-6A1-4V and porous coated. The material was chosen since its elastic modulus is almost half that of the Co-Cr-Mo alloy. One of the experimental implants remained unmodified. The other three experimental implants were modified as follows: The distal half of one of the implants was produced with a slot in a coronal plane of the distal stem. The third implant was fabricated with a hollow stem. The hole ran axially through the length of the shaft. The fourth implant was manufactured with an increasingly deep channel extending from below the proximal medial aspect to the distal tip 46 and was generally configured in accordance with FIG. 1 herein.

Figure 5:
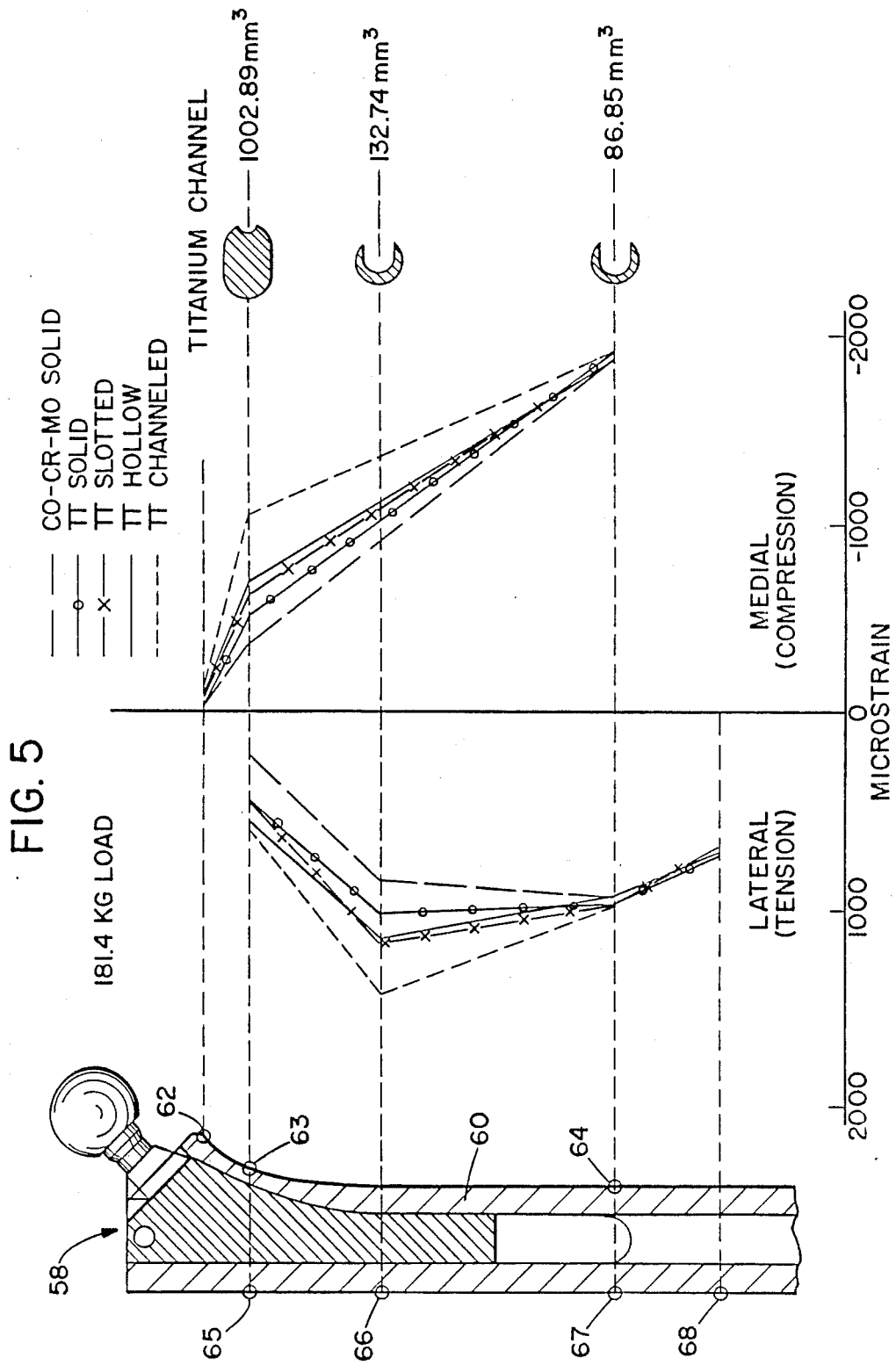
FIG. 5 is, in part, a schematic side elevation view, partly in section, of a femoral component embedded in a femur and, in part, a graph presenting the resultant microstrain exhibited by each of one standard and four experimental femoral components as they are subjected to stress.

For purposes of the investigation being described, a polysulfone analog femur was developed based on the mass properties of several nominally sized cadavaric femora. The analog femur approximated the flexural stiffness of an average sized natural femur. As indicated in FIG. 5 which is a schematic illustration of each of the test implants 58 and an associated resulting microstrain graph, the implant 58 is shown inserted into its mating analog femur 60. Seven strain gauges, numbered 62–68, consecutively, are located as illustrated on the femur and the section properties of each strain gauge location were calculated for each implant as shown.

After each implant was inserted into the analog femur, the latter, in turn, was mounted into a mechanical testing machine. Thereupon, the implant was loaded at the head and the femur was allowed to flex in an unrestricted fashion in a coronal plane using a hinge at the distal end of the femur. Strain gauges were checked for linearity at three load levels and each implant was loaded in an identical fashion to the three load levels. Gauge measurements for each gauge were recorded and converted to microstrain and the trends were perfectly consistent at each of the load levels. The conclusion was reached that the channeled implant was the most effective of the implants tested in increasing proximal femur strains, and that the channeled implant was particularly effective when applied to the lower modulus material, namely, the titanium alloy.

A bar chart presenting the identical information provided in FIG. 5, but in different form is presented in FIG. 6. Further, it will be noted that FIG. 5 also illustrates the shape of each cross section taken at the respective locations of the strain gauges 63, 65; 66; and 64, 67. It also presents the section modulus at each of these cross sectional locations.

Figure 7:
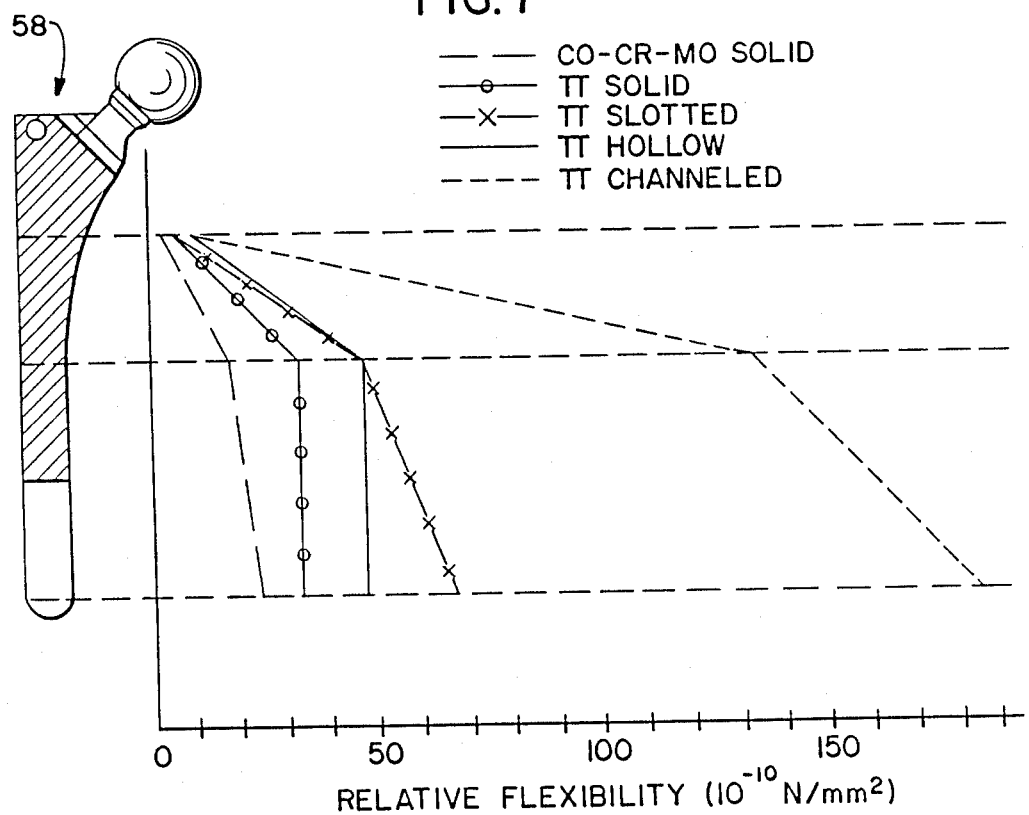
FIG. 7 is a graph illustrating the relative flexibility of the series of femoral componenets which were presented in FIGS. 5 and 6.

As was previously explained, the primary thrust of the invention is to prevent stress shielding at the proximal end of the femur 24 and, toward this end, to impart more stress and more strain into the femur. This desired result has been achieved as is seen in FIG. 7 which is illustrative of the relative flexibility of the test implant 58 at three of the cross sectional locations presented in the FIG. 5 graph. Specifically, the magnitude of the resultant values as determined by the strain gauges 63, 65, and 67 clearly demonstrate the effectiveness of the invention according to which the increased flexibility of the channeled stem results in significant increases in strain being imparted to the proximal portion of the femur.

While a preferred embodiment of the invention has been disclosed in detail, it should be understood by those skilled in the art that various other modifications may be made to the illustrated embodiment without departing from the scope of the invention as described in the specification and defined in the appended claims.

What is claimed is:

1. A component of an artificial joint for replacing a damaged natural joint in a skeletal structure of a body which includes a prosthesis having a first cooperating member to be secured to a first long bone having an intramedullary canal, the first cooperating member adapted to engage and being relatively movable with a second cooperating member of a second bone to permit relative movement between the first and second bones, comprising:

an elongated stem having a longitudinal axis lying generally in a coronal plane and being integral with the first cooperating member and receivable in the intramedullary canal of the first bone, said stem extending between proximal and distal ends and having a longitudinal channel generally lying in the coronal plane when said stem is implanted, the thickness of said stem laterally of said channel being variable between said proximal and distal ends so as to affect the moment of inertia at any given location along the length of said stem to thereby achieve a stem flexibility which substantially correlates to the flexibility of the first bone.

2. A component as set forth in claim 1 wherein a cross section of said stem lying in a plane transverse to the longitudinal axis thereof is substantially C-shaped in the lateral-medial direction; and wherein the maximum lateral-medial dimension of said stem is no more than 30% smaller than a similarly sized and shaped stem not formed with said channel.

3. A component as set forth in claim 1 which is composed of any one of titanium, titanium alloy, cobalt-chromium alloy, and composite materials.

4. In an artificial joint for replacing a damaged natural joint in a skeletal structure of a body which includes a prosthesis having a first cooperating member to be secured to a first long bone having an intramedullary canal, said first cooperating member adapted to engage and being relatively movable with a second cooperating member of a second bone to permit relative movement between the first and second bones, the improvement comprising:

an elongated stem having a longitudinal axis lying generally in a coronal plane and being integral with said first cooperating member and receivable in the intramedullary canal of the first bone, said stem extending between proximal and distal ends and having a longitudinal channel generally lying in the coronal place when said stem is implanted, the thickness of said stem laterally of said channel being variable between said proximal and distal ends so as to affect the moment of inertia at any given location along the length of said stem to thereby achieve a stem flexibility which substantially correlates to the flexibility of the first bone.

5. The improvement as set forth in claim 4 wherein a cross section of said stem lying in a plane transverse to the longitudinal axis thereof is substantially C-shaped in the lateral-medial direction; and wherein the maximum lateral-medial dimension of said stem is no more than 30% smaller than a similarly sized and shaped stem not formed with said channel.

6. The improvement as set forth in claim 4 wherein said stem is composed of any one of titanium, titanium alloy, cobalt-chromium alloy, and composite materials.

7. An artificial joint for replacing a damaged natural joint in a skeletal structure of a body comprising:

a ball member rotatably engageable with a cup shaped socket member to be secured to a first bone of the joint; and a mounting member including an elongated stem for securing said ball member to a second bone separate from the first bone, being a long bone with an intramedullary canal, said stem having a longitudinal axis lying generally in a coronal plane and being receivable in the intramedullary canal of the second bone, said stem extending from a proximal end adjacent said ball member to a distal end distant from said ball member, and having a longitudinal channel generally lying in the coronal plane when said stem is implanted in the intramedullary canal of the second bone, the thickness of said stem laterally of said channel being variable between said proximal and distal ends so as to affect the moment of inertia at any given location along the length of said stem to thereby achieve stem flexibility which substantially correlates to the flexibility of the second bone.

8. An artificial joint as set forth in claim 7 wherein a cross section of said stem lying in a plane transverse to the longitudinal axis thereof is substantially C-shaped in the lateral-medial direction; and wherein the maximum lateral-medial dimension of said stem is no more than 30% smaller than a similarly sized and shaped stem not formed with said channel.

9. An artificial joint as set forth in claim 7 wherein the first bone is the pelvis; and wherein the second bone is the femur; and wherein said ball member and said stem are parts of a femoral component of a hip prosthesis.

10. An artificial joint as set forth in claim 7 wherein said mounting member and said ball member are composed of any one of titanium, titanium alloy, cobalt-chromium alloy, and composite materials.

* * * * *